US012642907B2

(12) United States Patent
De Leon Hernandez

(10) Patent No.: US 12,642,907 B2
(45) Date of Patent: Jun. 2, 2026

(54) MANUAL AND BATTERY POWERED WOUND WASHING GUN

(71) Applicant: Mariana De Leon Hernandez, Miami Springs, FL (US)

(72) Inventor: Mariana De Leon Hernandez, Miami Springs, FL (US)

( * ) Notice: Subject to any disclaimer, the term of this patent is extended or adjusted under 35 U.S.C. 154(b) by 313 days.

(21) Appl. No.: 18/418,104

(22) Filed: Jan. 19, 2024

(65) Prior Publication Data

US 2025/0235602 A1 Jul. 24, 2025

(51) Int. Cl.
*A61M 3/02* (2006.01)

(52) U.S. Cl.
CPC ..................................... *A61M 3/02* (2013.01)

(58) Field of Classification Search
CPC .. A61M 2205/8206; A61M 2210/0625; A61M 3/02; A61M 3/0216; A61M 3/0258; A61M 3/0279; A61M 3/0283; A61M 2005/323; A61M 2005/3238; A61M 35/00; A61M 35/003; A61F 3/0229; A61F 2013/00536; A61D 7/00; A61D 5/50; B05B 11/11; B05B 11/1015; B05B 7/02
See application file for complete search history.

(56) References Cited

U.S. PATENT DOCUMENTS 3,452,745 A * 7/1969 Spitz ................... B05B 11/1015
601/161
5,097,540 A * 3/1992 Lovitt ................. A61M 3/0254
4/443

5,470,305 A * 11/1995 Arnett ................... A61M 1/774
601/161
6,293,929 B1 * 9/2001 Smith ................. A61M 3/0287
604/289
9,987,403 B2 * 6/2018 Kidman ............... A61M 3/022
2005/0236498 A1 * 10/2005 Cunningham ........ B01F 25/312
239/313
2006/0261087 A1 * 11/2006 Amron .................. F41B 9/0018
239/525
2007/0045446 A1 * 3/2007 Amron .................. F41B 9/0018
239/263.1
2008/0065001 A1 * 3/2008 DiNucci ............. A61M 3/0258
604/73
2009/0032618 A1 * 2/2009 Hornsby ............... B05B 1/3436
222/333
2010/0262073 A1 * 10/2010 Henniges ................ A61M 1/72
604/82

(Continued)

*Primary Examiner* — Michele Kidwell
(74) *Attorney, Agent, or Firm* — Ruben Alcoba, Esq.

(57) ABSTRACT

A manual and battery powered wound washing gun that is comprised of a gun housing that has a handle section and a barrel section, a reservoir that is housed within the barrel section, a battery that is housed within the housing, a pump that is operatively connected to the battery that is housed within the housing, an internal trigger mechanism that is a one way valve that is housed within the handle section, a nozzle that is attached to a front section of the barrel section, a first hose that is configured to inject a sterile liquid into the pump, a second hose that takes the sterile liquid into reservoir from the pump, a third hose that takes the sterile liquid from the reservoir to the internal trigger mechanism, a fourth hose that takes the sterile liquid to the nozzle from internal trigger mechanism.

6 Claims, 3 Drawing Sheets

(56)  References Cited

U.S. PATENT DOCUMENTS

| 2012/0032000 A1* | 2/2012 | Brunk | B05B 7/2421 239/337 |
| 2013/0066261 A1* | 3/2013 | Henniges | A61M 1/77 604/43 |
| 2015/0182685 A1* | 7/2015 | Henniges | A61M 1/72 604/151 |
| 2017/0252757 A1* | 9/2017 | Peterson | A01M 7/0046 |

* cited by examiner

MANUAL AND BATTERY POWERED WOUND WASHING GUN

BACKGROUND

The present invention is directed to a manual and battery powered wound washing gun.

The present device is a hydro-cleaning device that allows a user to wash a wound at either a set battery powered liquid release pressure or at a user manually applied liquid release pressure.

The inventor of the present invention is a physician that is presented with wounds daily. She recognizes the need of having a device that can automatically discharge a wash to wound at a set pressure and that can also discharge a wash at a variable pressure. Often, wounds that she treats require variable wash pressures at different sections of the wound.

The present device allows a physician to wash detritus from wounds safely. It also allows the physician to remove non-viable tissues and exudate from wounds. And it allows the physician to remove bacteria from a wound bed.

The device of the present invention allows a user to target a specific area of the wound that is to be washed. The targeted delivery of a wash may prevent cross-contamination of a patient being washed by the device.

The present invention is a cost-effective disposable wound washing gun that can be disposed after every use, if need be.

The wound washing gun of the present invention can be used in the following types of surgeries or procedures: traumatology, gynecology, orthopedics, neurology, gastroenterology, burn treatment, cosmetic surgeries, and for the treatment of any open wound that is to be washed.

The present device was developed to be a cost effective lightweight refillable wound washing gun that could be easily manipulated by the user.

SUMMARY

The present invention is a manual and battery powered wound washing gun that allows a user to wash a wound either by using a battery powered force or a user applied force.

The manual and battery powered wound washing gun is comprised of a gun housing that has a handle section and a barrel section, a reservoir that is housed within the barrel section, a battery that is housed within the housing, a pump that is operatively connected to the battery that is housed within the housing, an internal trigger mechanism that is a one way valve that is housed within the handle section, a nozzle that is attached to a front section of the barrel section, a first hose that is configured to inject a sterile liquid into the pump, a second hose that takes the sterile liquid into reservoir from the pump, a third hose that takes the sterile liquid from the reservoir to the internal trigger mechanism, a fourth hose that takes the sterile liquid to the nozzle from internal trigger mechanism. The nozzle of the present invention is designed to receive three different liquid guiding extensions.

In a preferred embodiment, the gun housing is ergonomic and is latex free.

An object of the present invention is to provide a manual and battery powered wound washing gun that is used to wash a wound.

Another object of the present invention is to provide a manual and battery powered wound washing gun that is lightweight.

Yet another object of the present invention is to provide a manual and battery powered wound washing gun that is disposable.

Yet still another object of the present invention is to provide a manual and battery powered wound washing gun that is latex free.

A further object of the present invention is to provide a manual and battery powered wound washing gun that will prevent cross contamination when an open wound is washed.

A still further object of the present invention is to provide a manual and battery powered wound washing gun that can be used to wash delicate wounds.

Yet another object of the present invention is to provide a manual and battery powered wound washing gun that will remove exudate from a wound.

Yet still another object of the present invention is to provide a manual and battery powered wound washing gun that will not alter the granulation process of a wound.

A further object of the present invention is to provide a manual and battery powered wound washing gun that can be connected to sterile liquid carrying containers, bottles, or bag solutions.

Another object of the present invention is to provide a manual and battery powered wound washing gun that will be used to remove non-viable tissues with any washing technique and with any antiseptic solution.

BRIEF DESCRIPTION OF THE DRAWINGS

These and other features, aspects, and advantages of the present invention will become better understood with regards to the following description, appended claims, and drawings where:

DESCRIPTION

Figure 1:
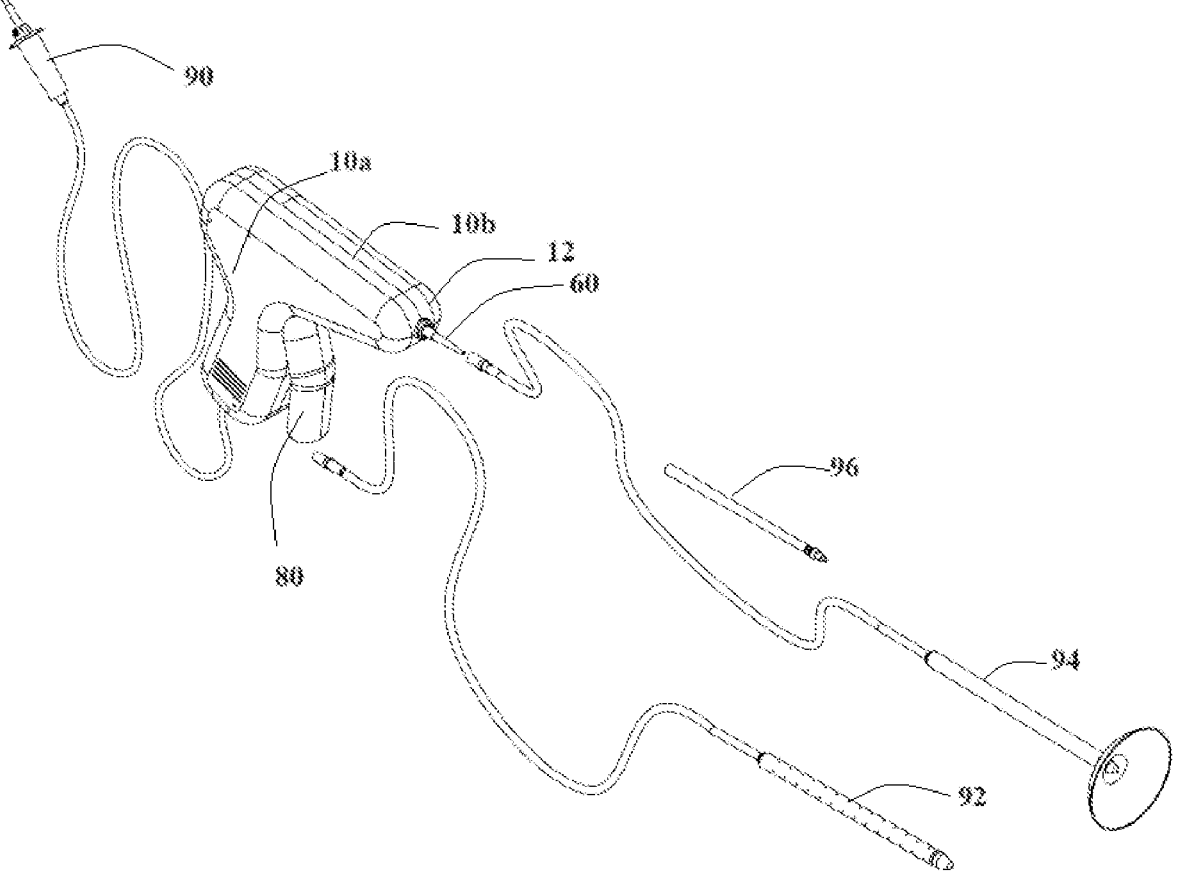
FIG. 1 shows a downward perspective view of the present invention.
Figure 2:
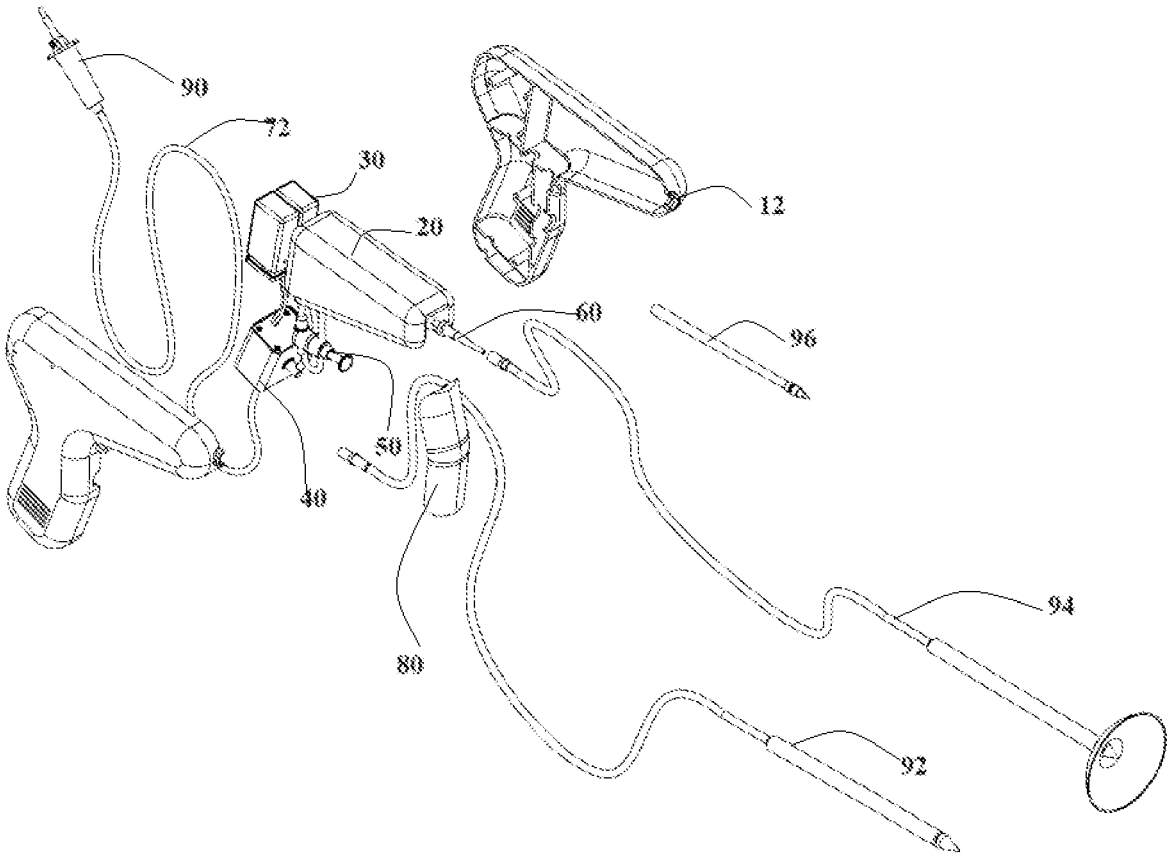
FIG. 2 shows a downward exploded perspective view of the present invention.
Figure 3:
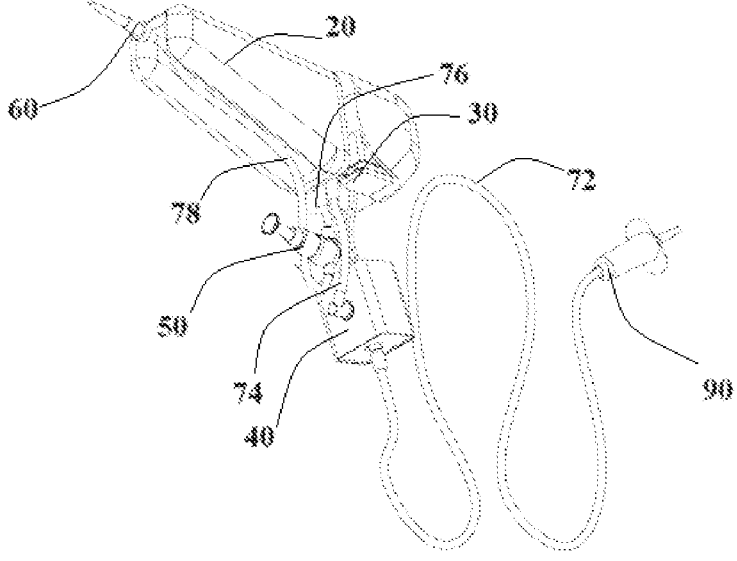
FIG. 3 shows a upward perspective view of the connections of the present invention.

As seen in FIGS. 1-3, the present invention is a manual and battery powered wound washing gun that allows a user to wash a wound of a patient.

The manual and battery powered wound washing gun comprises a gun housing 10 that has a handle section 10a and a barrel section 10b. A reservoir 20 that is housed within the barrel section 10b. A battery 30 that is housed within the housing 10. A pump 40 that is operatively connected to the battery 30 that is housed within the housing 10. An internal trigger mechanism 50 that is a one-way valve that is housed within the handle section 10a. A nozzle 60 that is attached to a front section 12 of the barrel section 10b. A first hose 72 that is configured to inject a sterile liquid into the pump 40. A second hose 74 that takes the sterile liquid into reservoir 20 from the pump 40. A third hose 76 that takes the sterile liquid from the reservoir 20 to the internal trigger mechanism 50. And, a fourth hose 78 that takes the sterile liquid to the nozzle 60 from internal trigger mechanism 50.

In an embodiment of the present invention, the manual and battery powered wound washing gun comprises of a trigger actuator 80 that attached to the internal trigger mechanism 50.

In another embodiment of the present invention, the manual and battery powered wound washing gun comprises of an infusion tip 90 that attaches to the first hose 72.

In yet another embodiment of the present invention, the manual and battery powered wound washing gun comprises of an irrigation tip extension 92 that attaches to the nozzle 60.

In yet still another embodiment of the present invention, the manual and battery powered wound washing gun comprises of a shielded tip extension 94 that attaches to the nozzle 60.

In still another embodiment of the present invention, the manual and battery powered wound washing gun comprises of a short tip extension 96 that attaches to the nozzle 60.

An advantage of the present invention is that it provides a manual and battery powered wound washing gun that is used to wash a wound.

Another advantage of the present invention is that it provides a manual and battery powered wound washing gun that is lightweight.

Yet another advantage of the present invention is that it provides a manual and battery powered wound washing gun that is disposable.

Yet still another advantage of the present invention is that it provides a manual and battery powered wound washing gun that is latex free.

A further advantage of the present invention is that it provides a manual and battery powered wound washing gun that prevents cross contamination when an open wound of a patient is washed.

A still further advantage of the present invention is that it provides a manual and battery powered wound washing gun that is used to wash delicate wounds.

Yet another advantage of the present invention is that it provides a manual and battery powered wound washing gun that removes exudate from a wound.

Yet still another advantage of the present invention is that it provides a manual and battery powered wound washing gun that does not alter the granulation process of a wound.

A further advantage of the present invention is that it provides a manual and battery powered wound washing gun that connects to sterile liquid carrying containers, bottles, or bag solutions.

Another advantage of the present invention is that it provides a manual and battery powered wound washing gun that removes non-viable tissues with any washing technique and with any antiseptic solution.

While the inventor's description contains many specificities, these should not be construed as limitations of the manual and battery powered wound washing gun, but rather as an exemplification of several preferred embodiments thereof, any other variations may be possible. Accordingly, the scope should be determined not by the embodiments illustrated, but by the specification, the drawings, and the claims and any legal equivalent thereof.

What is claimed is:

1. A manual and battery powered wound washing gun that allows a user to wash a patient wound, the manual and battery powered wound washing gun comprises:

a gun housing that has a handle section and a barrel section;

a reservoir that is housed within the barrel section;

a battery that is housed within the housing;

a pump that is operatively connected to the battery that is housed within the housing;

an internal trigger mechanism that is a one way valve that is housed within the handle section;

a nozzle that is attached to a front section of the barrel section;

a first hose configured to inject a sterile liquid into the pump;

a second hose configured to convey the sterile liquid into reservoir from the pump;

a third hose configured to convey the sterile liquid from the reservoir through the handle section of the housing to the internal trigger mechanism; and a fourth hose configured to convey the sterile liquid from the internal trigger mechanism to the nozzle.

2. The manual and battery powered wound washing gun that allows the user to wash the patient wound of claim 1, the manual and battery powered wound washing gun comprises of a trigger actuator that attached to the internal trigger mechanism.

3. The manual and battery powered wound washing gun that allows the user to wash the patient wound of claim 2, the manual and battery powered wound washing gun comprises of an infusion tip extension that attaches to the first hose.

4. The manual and battery powered wound washing gun that allows the user to wash the patient wound of claim 3, the manual and battery powered wound washing gun comprises of an irrigation tip extension that attaches to the nozzle.

5. The manual and battery powered wound washing gun that allows the user to wash the patient wound of claim 3, the manual and battery powered wound washing gun comprises of a shielded tip that attaches to the nozzle.

6. The manual and battery powered wound washing gun that allows the user to wash the patient wound of claim 3, the manual and battery powered wound washing gun comprises of a short tip extension that attaches to the nozzle.

* * * * *